United States Patent [19]

Campbell

[11] 4,024,142

[45] May 17, 1977

[54] QUINOXALINE DERIVATIVES AS IMMUNE REGULANTS

[75] Inventor: Jack B. Campbell, Indianapolis, Ind.

[73] Assignee: Eli Lilly and Company, Indianapolis, Ind.

[22] Filed: July 16, 1975

[21] Appl. No.: 596,543

[52] U.S. Cl. .......................... 260/250 Q; 260/266; 424/250

[51] Int. Cl.² ...................................... C07D 241/42

[58] Field of Search ................ 260/250 Q, 250 QN

[56] References Cited

UNITED STATES PATENTS

| | | | |
|---|---|---|---|
| 2,046,254 | 6/1936 | Eckert | 260/250 Q |
| 3,005,789 | 10/1961 | Bloom | 260/250 Q |
| 3,481,931 | 12/1969 | Vivian | 260/250 QN |

OTHER PUBLICATIONS

Gordienko et al., Chem. Abs. 72, 99718m (1969).
Guha et al., J. Indian Chem. Soc. 48, 1011 (1971).
Kiprianov, Chem. Abs. 49, 11667f (1954).

*Primary Examiner*—Donald G. Daus
*Assistant Examiner*—Mark L. Berch
*Attorney, Agent, or Firm*—William B. Scanlon; Everet F. Smith

[57] ABSTRACT

Novel quinoxaline derivatives, useful as immune regulatory agents capable of altering the immune response in mammals.

1 Claim, No Drawings

QUINOXALINE DERIVATIVES AS IMMUNE REGULANTS

BACKGROUND OF THE INVENTION

Recently, immune suppressant agents have come into prominence because of their use during transplants of organs from one human to another, and in particular in connection with organ transplant operations such as heart and kidney transplants. It is part of the defense mechanism of humans to remove foreign antigens (in this case, produced by the transplanted organ) by the immune reaction. Thus, in all of the organ transplant operations, it has been necessary to give large doses of an immune suppressant prior to the operation and continuing thereafter in order to prevent the host from rejecting the donor organ.

The immune response is composed of a sequence of cellular transformations and biochemical events leading to a bimodal response to foreign substances (antigens). Cells which are to participate in the response evolve from stem cells which originate in the bone marrow and are seeded out to the peripheral lymphoid organs. From these latter sites, following antigenic stimulus, the body's response is mounted in the form of plasma cells (which produce antibody) and specific immune lymphocytes. Antibody is released into the circulatory system and thus may act at a distance from the producing cell (humoral immunity). Specific immune lymphocytes also enter the circulatory system and act at the site of injury (cellular immunity). The reaction of antibody with antigen triggers the release of histamine from basophilic leucocytes; histamine, in turn, alters the permeability of blood vessels, speeding the influx of both antibody and specific immune lymphocytes into the sites of injury. Thus, the immune response is composed of a series of biochemical events in a sequence of cells at various sites in the body. It can be altered — suppressed, in the case of the compounds herein discussed — at a number of biochemical or cellular developmental sites.

Antihistamines only affect a secondary reaction in the immune response, having no direct effect on antibody-producing cells or on specific immune lymphocytes. A number of agents, currently in use as immunosuppressive drugs, act further back in the chain of events called herein the immune response. Certain anti-inflammatory steroids, e.g., cortisone, suppress production of antibody and specific immune lymphocytes, but also radically deplete normal lymphoid tissue and have other undesirable side effects. Certain antineoplastic drugs e.g., azathioprine, cyclophosphamide, and methotrexate, are employed as immunosuppressives, but they also deplete normal lymphoid tissue and radically depress other bone-marrow-derived cells. The general cytotoxicity of the latter drugs is to be expected in view of their having been selected on the basis of toxicity against a spectrum of cell types.

It is an object of this invention to provide novel compounds which alter the immune response in mammals by acting on cells functioning in the immune response, but which avoid certain side-effects and other undesirable attributes of compounds currently available as immune regulants.

Quinoxaline compounds are known in the art and can be prepared by the condensation of an aromatic o-diamine with a 1,2-diketone. The general preparation of quinoxalines is described in "The Chemistry of Heterocyclic Compounds," Vol. 5, Chapters 24–38 A. Weissberger, Ed., (Interscience Publishers, Inc. New York, 1953). When the diketones acenaphthalenequinone or phenanthrenequinone are condensed with o-phenylenediamines, the products are respectively acenaphtho[1,2-b]quinoxalines or dibenzo[a,c]phenazines. Acenaphtho[1,2-b]quinoxaline is described in Ber. 43, 441 (1910) and dibenzo[a,c]phenazine is described in Ann. 237, 341 (1887).

The acenaphtho[1,2-b]quinoxalines are named and numbered according to the Ring Index, The American Chemical Society, number 5998 and the dibenzo[a,c]phenazines are named and numbered according to the Ring Index, number 6221, as follows:

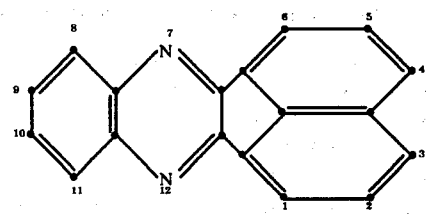

Acenaphtho[1,2-b]quinoxalines

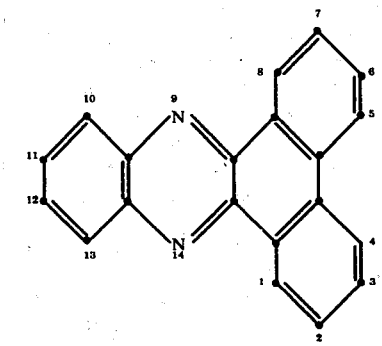

Dibenzo[a,c]phenazines

SUMMARY OF THE INVENTION

This invention provides novel condensed quinoxalines represented by the formula

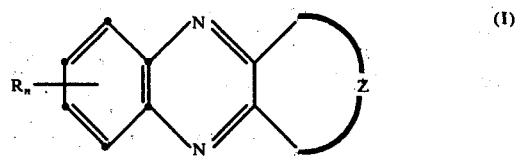

wherein each R is independently amino, chloro, methoxy, phenyl or trifluoromethyl, $n$ is 1 or 2; and Z is

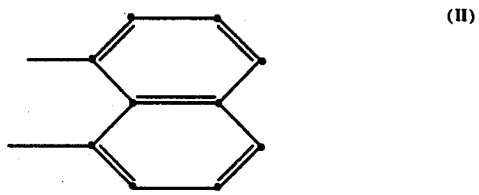

or

-continued

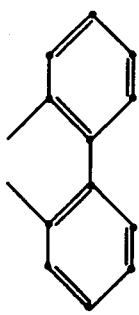

(III)

subject to the limitation that R is other than chloro or phenyl when Z is III.

The dibenzo[a,c]phenazine compounds wherein Z is III are preferred over the acenaphtho[1,2-b]quinoxaline compounds wherein Z is II and the trifluoromethyl compounds are most preferred.

Phenazines and quinoxalines represented by I above are useful as immune regulatory agents capable of altering the immune response in mammals.

DETAILED DESCRIPTION AND PREFERRED EMBODIMENTS

The compounds of the invention represented by the formula I above are prepared by the condensation of suitable aromatic diamines with the appropriate 1,2-diketones. The reaction of diamines with phenenthrenequinone provides the dibenzo(a,c)phenazine compounds and the condensation of diamines with acenaphthenequinone yields the acenaphtho[1,2-b]quinoxalines. The ketone reactants are commercially available.

Alternatively, the quinoxaline and phenazine compounds of this invention can be prepared from the appropriate o-nitroaniline precursors of the required aromatic o-diamines. By this procedure, the o-nitroanilines are hydrogenated catalytically to provide the corresponding o-diamines in situ for condensation with the appropriate ketone. Suitable hydrogenation catalysts include Raney nickel, 5 percent palladium-on-carbon, platinum oxide, and the like. The nitroaniline can be hydrogenated in the presence of the ketone reactant and the condensation is completed by heating at elevated temperatures. Solvents which are inert to hydrogenation conditions such as ethanol or tetrahydrofuran can be suitably employed as the reaction medium. Instead of the o-nitroaniline, the appropriate o-phenylenediamine can be employed in the condensation reaction. Generally in the practice of this invention, molar equivalents of the o-phenylenediamine or o-nitroaniline reactant and diketone are employed. However, an excess of either reactant can be used if desired without adverse effect on the yield. The quinoxaline or phenazine product can be recovered by evaporation of the solvent and purification can be accomplished by conventional methods such as crystallization or chromatography.

The o-nitroaniline or o-phenylenediamine compounds which are required as reactants are either commercially available or can be prepared by known methods of amination, nitration or reduction of suitable aromatic precursors. The required benzotrifluoride reactants can be prepared by the fluorination of the corresponding benzoic acids with sulfur tetrafluoride.

The compounds of this invention were tested for their ability to reduce antibody production by the following means.

TEST METHODS

Groups of five 20-gram, male, random-bred, Swiss mice received intravenous injections of $5 \times 10^7$ sheep red blood cells. The cells for these injections were prepared from lamb's blood (collected in Alsever's solution) by washing three times with 0.85 percent saline and resuspending in 0.85 percent saline. Nine daily doses of the compounds, solubilized in polyethylene glycol 400, were administered orally in 0.1 ml doses, commencing three days prior to red blood cell injection. Several dose levels of each drug were employed, at 2-fold increments. A control group of mice, receiving a red blood cell injection and nine daily doses of vehicle instead of drug, was included. Six days after the antigen injections, the mice were bled by cardiac puncture and the sera from each 5-mouse group pooled. The serum pools, following complement inactivation, were assayed for hemagglutinin content by standard procedures, utilizing mixture of serial 2-fold saline dilutions of the test sera with 0.5 percent sheep red blood cell suspensions in plastic depression trays. Following incubation of the trays for 3 hours at 37° C., the hemagglutination patterns were graded. A 4-fold (75 percent) or greater antibody reduction (in the test serum as compared with the control serum) was considered significant. The results were expressed as the lowest drug dose producing 75 percent or greater antibody reduction.

The effect of subcutaneous administration was determined by substituting subcutaneous injections for the oral treatment in the preceding procedures. The effect of intraperitoneal administration was determined in mice receiving intraperitoneal red blood cell antigen and two doses of drug, administered intraperitoneally 48 hours before and after antigen injection. Suspensions of the drugs in saline containing 0.125 percent "Methocel" and 0.2 "Emulphor" were employed in the parenteral treatments. The bleeding and antibody determinations were performed as indicated above.

The results of testing the quinoxaline and phenazine compounds of this invention for their ability to reduce antibody production are summarized in Tables I and II. The immunosuppressive endpoint is defined as set forth above as the lowest drug dose which produces at least a 75 percent reduction of antibody formation. Azathioprine (IMURAN), which is used for clinical immunosuppression, has an immunosuppressive endpoint at 100 mg/kg by this test. It will be noted the known prior art compounds, acenaphtho[1,2-b]quinoxaline and dibenzo[a,c]phenazine, have minimal or insignificant activity (Tables I and II).

Table I

| | Dibenzo(a,c)phenazine Compounds | |
|---|---|---|
| $R_n$ Substituent(s) | Immunosuppressive IP × 2 vs IP | endpoint (mg/kg)* Oral × 9 vs IV |
| hydrogen | 100 | >100    > |

Table I-continued

| $R_n$ Substituent(s) | Dibenzo(a,c)phenazine Compounds Immunosuppressive IP × 2 vs IP | endpoint (mg/kg)* Oral × 9 vs IV |
| --- | --- | --- |
| 11-trifluoromethyl- | 0.8 | 3.1 |
| 11-amino- | — | 3.1 |
| 10-trifluoromethyl- | — | 6.2 |
| 10-amino-12-trifluoromethyl | — | 12.5 |
| 11-methoxy- | 12.5 | >100 > |

*Treatment schedule indicated in sub-heading, e.g. "IP × 2 vs IP" indicates 2 doses given intraperitoneally, 48 hr before and after sheep red blood cell antigen, which was administered intraperitoneally. Oral therapy given daily for 9 days, commencing 3 days prior to intravenous antigen. Mice bled on 6th post-antigen day for hemagglutinin (HA) assay. Endpoint determined by lowest drug dose producing 75 percent or greater suppression of HA, as compared with untreated control value.

Table II

| $R_n$ Substituent(s) | Acenaphtho[1,2-b]quinoxaline Compounds Immunosuppressive IP × 2 vs IP | endpoint (mg/kg)* Oral × 9 vs IV |
| --- | --- | --- |
| hydrogen | — | >100 |
| 8-trifluoromethyl | — | >100 |
| 9-trifluoromethyl- | 6.2 | 25 |
| 9-chloro- | 12.5 or less | 25 |
| 9-methoxy- | — | 25 |
| 9-phenyl- | 50 or less | 50 |
| 8-chloro- | 50 | >100 |

*Treatment schedule indicated in sub-heading, e.g. "IP × 2 vs IP" indicates 2 doses given intraperitoneally, 48 hr before and after sheep red blood cell antigen, which was administered intraperitoneally. Oral therapy given daily for 9 days, commencing 3 days prior to intravenous antigen. Mice bled on 6th post-antigen day for hemagglutinin (HA) assay. Endpoint determined by lowest drug dose producing 75 percent or greater suppression of HA, as compared with untreated control value.

The compounds were tested further by a modified serum assay procedure as described hereinbelow.

INDIVIDUAL SERUM ASSAY PROCEDURE

In these tests, the procedure described above was modified by the use of 10-mouse groups, rather than 5-mouse groups. The mice were bled as before, but the sera were titered individually rather than as a pool. Mean hemagglutinin values ($\log_2$) ± S.E. were calculated for each 10-mouse group and $p$ values (by Student's Test), in comparison with the control group, were determined. The lowest drug dose significantly ($p < 0.01$) lowering antibody titer defined the endpoint. In some instances, drugs were administered in 10, rather than 9, daily doses; in these instances, the mice were bled on 7th, rather than the 6th, post-antigen day. Typical results obtained in the individual serum assay test with representative compounds of the invention are summarized in Table III.

mouse strain was tested by a method called the graft-versus-host reaction.

GRAFT-VERSUS-HOST (GVH) REACTION

In this test, parental (C57BL) mouse spleen cells are injected into mice of an $F_1$ hybrid strain (C57BL × C3H). The recipient mice do not reject the injected spleen cells, since the hybrid recognizes C57BL-related antigens from its homozygous parent as "self." The injected cells, however, mount a reaction to the recipient's tissue due to the foreign C3H-derived antigens. As a consequence, the recipient's spleen becomes enlarged. Immunosuppression prevents or reduces this enlargement. Thus, spleen weights provide a measure of the GVH reaction and its reduction under immunosuppression.

A modification of Simonsen's original procedure (Ann. N.Y. Acad. Sci. 73:834, 1958) was employed. Large crops of spleen cells were obtained, without the generally employed manual teasing of spleens, by using Waring blendors with the cutting blades reversed. Two six-second blending periods buffeted the spleens (25 C57BL spleens in 25-ml saline) sufficiently to free the cells from the connective tissue. Cell suspensions prepared in this fashion were standardized, by means of Levy-Hausser chamber counts, to contain $6 \times 10^8$ nucleated cells per ml. Groups of five 16–18 gram C57BL × C3H mice were injected intraperitoneally with 1 ml of the donor cell suspension. Treatment, by the subcutaneous route in 0.2 ml, was instituted 3 days prior to cell injection and continued daily for 13 days. Control animals received only cells and vehicle. The spleens were removed and weighed 10 days following cell injection. The results were expressed as mg spleen/gram body weight.

Table III

Immunosuppressive Activity of Compounds
(Individual Serum Assay Procedure)

| Compound | Route | Doses | Vehicle | Endpoint Dose (p <0.01) in mg/kg. |
| --- | --- | --- | --- | --- |
| 11-(trifluoromethyl)-dibenzo(a,c)phenazine | Oral | 9 | PEG 400 | 0.4 |
| '' | Oral | 10 | PEG 400 | 0.2 |
| '' | Oral | 9 | Methocel-E | 0.8 or less |
| '' | Oral | 10 | Methocel-E | 0.4 |
| '' | Oral | 10 | Corn Oil | 0.8 or less |
| '' | SC | 10 | Methocel-E | 0.1 |
| 10-(trifluoromethyl)-dibenzo(a,c)phenazine | Oral | 9 | PEG 400 | 0.8 or less |
| 9-(trifluoromethyl)-acenaphtho[1,2-b]-quinoxaline | Oral | 9 | PEG 400 | 3.1 |

The immunosuppressive action of the compounds of the invention in reducing spleen-enlargement in mice injected with spleen cells of a lymphoid graft-inducing Since the injection of syngeneic, i.e., C57BL × C3H, cells into the recipient mice produces a minor degree of splenomegaly, spleen weights of such animals were used to define 100% suppression of the GVH component in calculating percents of inhibition produced by the immunosuppressive compounds. The method of calculation is illustrated in the following example from mice treated with a reference immunosuppressive compound:

| Reference Compound Treatment | Mg Spleen/g Body Wt. ± S.E.* | Percent Inhibition** |
| --- | --- | --- |
| 12.5 mg/Kg × 13 | 6.86 ± 0.80*** | 74 |
| None (GVH Control) | 11.55 ± 1.01 | 0 |
| None (Syn. Control) | 5.20 ± 0.37 | 100 |
| None (Normal Control) | 4.16 ± 0.17 | — |

*Mean values from groups of 5 mice.

** $\left(\dfrac{\text{GVH Control - Treated}}{\text{GVH Control - Syn. Control}}\right) x =$ Percent Inhibition

***p <0.01, compared with GVH control

Since in practice it was found that both syngeneic and normal controls varied only slightly from test to test, a composite value (4.8), derived from recalculating four separate syngeneic control groups (5.20 ± 0.37, 4.99 ± 0.39, 4.42 ± 0.13, 4.66 ± 0.12) as a 20-mouse group was used in the calculations. The results obtained in the graft-versus-host reaction with the compounds of the invention are summarized in Table IV.

Table IV

Effect of Compounds on GVH Reaction

| Drug | Dose (mg/kg × 13) | Mg Spleen/g Body Wt. S.E.* | Percent Inhibition** |
| --- | --- | --- | --- |
| 11-(trifluoromethyl)-dibenzo(a,c)phenazine | 80 | 4.72 ± 0.26 | 101.5 |
| 11-(trifluoromethyl)-dibenzo(a,c)phenazine | 20 | 5.65 ± 1.00 | 83.6 |
| 11-(trifluoromethyl)-dibenzo(a,c)phenazine | 5 | 5.68 ± 0.26 | 83.0 |
| 9-(trifluoromethyl)-acenaphtho[1,2-b]-quinoxaline | 80 | 5.00 ± 0.19 | 96.1 |
| 9-(trifluoromethyl)-acenaphtho[1,2-b]-quinoxaline | 20 | 4.67 ± 0.17 | 102.5 |
| 9-methoxyacenaphtho-[1,2-b]quinoxaline | 20 | 7.57 ± 0.69 | 46.4 |
| 9-methoxyacenaphtho-[1,2-b]quinoxaline | 20 | 7.35 ± 0.61 | 50.7 |
| Control | — | 9.97 + 0.49 | |

*Mean values from groups of 5 mice.

** $\left(\dfrac{\text{GVH Control - Treated}}{\text{GVH Control - Sym. Control}}\right) x =$ percent inhibition By virtue of their ability to suppress the immune response, the quinoxaline and phenazine compounds of this invention are suitable for pretreating patients undergoing organ transplant surgery. In addition to their use in organ transplant operations, immune regulating agents are also useful in various diseases of little-understood etiology, denominated generically as "auto-immune" diseases. These diseases include: auto-immune hemolytic anemia, idiopathic thrombocytopenic purpura, lupus erythematosus, lupoid hepatitis, lupus nephritis, glomerulonephritis, the nephrotic syndrome, Goodpasture's syndrome, Wegener's granulomatosis, schleroderma, Sezary's disease, psoriasis, uveitis, rheumatoid arthritis, ulcerative colitis, tthyroiditis and mumps orchitis. Auto-immune suppressant agents, such as azathiaprene, generally may be more or less useful in the treatment of the above diseases depending upon the degree to which the disease is dependent upon an auto-immune mechanism.

Routes of administration of the novel quinoxaline and phenazine compounds include oral and subcutaneous routes. For oral administration, the immune suppressent can be dissolved or suspended in polyethylene glycol. Aqueous vehicles, to which may be added surface-active agents, are also useful. For subcutaneous injection an isotonic solution is used. The immune-suppressant agent is present in the particular vehicle at the rate of from 1 to 200 mg/ml.

The following examples are further illustrative of the methods, intermediates and preparation of the compounds of the invention.

EXAMPLE 1

Preparation of 11-(Trifluoromethyl)dibenzo[a,c]phenazine

One tenth mole, 20.6 g., of 4-amino-3-nitrobenzotrifluoride was hydrogenated at room temperature in 100 ml. of 2B ethanol with 1.5 g. of palladium-on-carbon (5 percent) at 50 psi. Three equivalents of hydrogen were adsorbed and and temperature rose to 70° C. The catalyst was filtered and the filtrate was added to a warm suspension of 20.8 g. (0.10 m) of phenanthrenequinone in 2 l of ethanol with stirring.

Upon addition of the 3,4-diaminobenzotrifluoride solution, the reactants went into solution and soon after product began to precipitate. The reaction was completed by heating at reflux for about one hour. The precipitated product was collected by filtration to give about 27.8 g. (80 percent yield) of 11-(trifluoromethyl)dibenzo[a,c]phenazine, mp = 190°–192° C.

Analysis $C_{21}H_{11}F_3N_2$ MW 348. Calcd: C, 72.41; H, 3.18; N, 8.04; Found: C, 72.39; H, 3.05; N, 8.21.

EXAMPLES 2-5

Preparation of Condensed Quinoxalines

When 0.05 mole each of 3-nitro-4-biphenylamine and acenaphthenequinone were reacted by the method of Example 1, 13.2 g. (80 percent yield) of 9-phenylacenaphtho[1,2-b]quinoxaline, mp = 208°–210° C. were obtained.

Analysis $C_{24}H_{14}N_2$ MW 330. Calcd: C, 87.25; H, 4.27; N, 8.48; Found: C, 86.98; H, 4.24; N, 8.19.

When 0.05 mole each of 4-methoxy-2-nitroaniline and acenaphthenequinone were reacted by the method of Example 1, 12.9 g (91 percent yield) of 9-methoxyacenaphtho[1,2-b]-quinoxaline, mp = 194°–195° C. were obtained.

Analysis $C_{19}H_{12}N_2O$ MW 284. Calcd: C, 80.26; H, 4.25; N, 9.85; Found: C, 79.99 H, 4.37; N, 10.01.

When 0.12 mole each of 2,4-dichloro-6-nitroaniline and phenanthrenequinone were reacted by the method of Example 1, 24 g. (81 percent yield) of 10,12-dichlorodibenzo[a,c]phenazine, mp = 221°–222° C. (acetone), were obtained.

Analysis $C_{20}H_{10}Cl_2N_2$ MW 349. Calcd: C, 68.78; H, 2.89; N, 8.08; Found: C, 69.05; H, 2.92; N, 8.15.

When 0.14 mole each of 3,4-dichloro-6-nitroaniline and phenanthrenequinone were reacted by the method of Example 1, 48.8 g. (99.9 percent yield) of 11,12-dichlorodibenzo[a,c]phenazine, mp = 263°–264° C. (DMF), were obtained.

Analysis $C_{20}H_{10}Cl_2N_2$ MW 349. Calcd: C, 68.78; H, 2.89; N, 8.08; Found: C, 68.93; H, 2.85; N, 8.30.

EXAMPLE 6

Preparation of 10-(Trifluoromethyl)dibenzo[a,c]phenazine

A. 2-Chloro-3-nitrobenzotrifluoride

Nine grams (0.05m) of 2-chloro-3-nitrobenzoic acid, 27 g. (0.25m) of sulfur tetrafluoride and 5 g. of anhydrous hydrogen fluoride were heated in a sealed autoclave at 150° C. for 16 hours. After cooling and venting, the reaction mixture was taken up in ethyl acetate. The ethyl acetate solution was washed successively with dilute sodium hydroxide and water. The ethyl acetate phase was dried and evaporated in vacuo to yield crude 2-chloro-3-nitrobenzotrifluoride.

B. 2-Amino-3-nitrobenzotrifluoride

Eleven and two tenths grams (0.05m) of 2-chloro-3-nitrobenzotrifluoride, 200 ml. of liquid ammonia and 200 ml. of 2B ethanol were heated in a sealed autoclave at 100° C. for 4 hours. After cooling and venting, the reaction mixture was diluted with water. The aqueous mixture was extracted with ethyl acetate. The ethyl acetate phase was washed with water, dried, and was evaporated in vacuo to yield crude 2-amino-3-nitrobenzotrifluoride.

C. 10-(Trifluoromethyl)dibenzo[a,c]phenazine

When 0.034 mole each of 2-amino-3-nitrobenzotrifluoride and phenanthrenequinone were reacted by the method of Example 1, 9 g. (76 percent yield) of 10-(trifluoromethyl)dibenzo[a,c]phenazine, mp = 195°–196° C., were obtained.

Analysis $C_{21}H_{11}F_3N_2$ MW 348. Calcd: C, 72.41; H, 3.18; N, 8.04; Found: C, 72.24; H, 3.29; N, 7.97.

EXAMPLE 7

Preparation of 10-Amino-12-(trifluoromethyl)benzo[a,c]phenazine

A. 4-Chloro-3,5-dinitrobenzotrifluoride

One tenth mole, 25 g. of 4-chloro-3,5-dinitrobenzoic acid, 54 g. (0.5m) of sulfur tetrafluoride and 10 g. of anhydrous hydrogen fluoride were heated in a sealed autoclave at 150° C. for about 16 hours. After cooling and venting, the reaction mixture was taken up in ethyl acetate. The ethyl acetate phase was washed successively with dilute sodium hydroxide and water. The ethyl acetate solution was dried and evaporated in vacuo to yield crude 4-chloro-3,5-dinitrobenzotrifluoride.

B. 4-Amino-3,5-dinitrobenzotrifluoride

Twent-six grams (0.096m) of crude 4-chloro-3,5-dinitrobenzotrifluoride, 150 ml. of liquid ammonia and 150 ml. of 2B ethanol were heated in a sealed autoclave at 100° C. for about 4 hours. After cooling and venting, the reaction mixture was taken up in ethyl acetate. The ethyl acetate phase was washed with water. The ethyl acetate solution was dried and evaporated in vacuo to yield crude 4-amino-3,5-dinitrobenzotrifluoride.

C. 10-Amino-12-(trifluoromethyl)dibenzo[a,c]-phenazine

Twelve and five tenths grams (0.05m) of 4-amino-3,5-dinitrobenzotrifluoride, and 10.4 g. (0.05m) of phenanthrenequinone were reacted by the method of Example 1, to provide 11.8 g. (66 percent) of 10-amino-12-(trifluoromethyl)dibenzo[a,c]phenazine, mp = 194°–195° C.

Analysis $C_{21}H_{12}F_3N_3$ MW 363. Calcd: C, 69.42; H, 3.33; N, 11.57; Found: C, 69.22; H, 3.48; N, 11.28.

EXAMPLE 8

Preparation of 9-(Trifluoromethyl)acenaphtho[1,2-b]quinoxaline

Acenaphthenequinone, 9.1 g. (0.05m), and 10.3 g. (0.05m) of 4-amino-3-nitrobenzotrifluoride were hydrogenated at room temperature in 125 ml. of 2B ethanol with 2.5 g. of palladium-on-carbon (5 percent) at 50 psi. After 4 hours three equivalents of hydrogen were absorbed and the temperature rose to 40° C. The catalyst was filtered and the filtrate was diluted with 1.2 l of ethanol. The reaction was completed by refluxing the ethanolic solution for about one hour. The precipitated product was collected to yield about 8 g. (50 percent yield) of 9-(trifluoromethyl)acenaphtho[1,2-b]quinoxaline, mp = 185°–186° C.

Analysis $C_{19}H_9F_3N_2$ MW 322. Calcd: C, 70.81; H, 2.81; N, 8.69; Found: C, 70.64; H, 3.01; N, 8.97.

EXAMPLE 9

Preparation of 11-Aminodibenzo[a,c]phenazine

A. 11-Nitrodibenzo[a,c]phenazine

One tenth mole, 15.3 g., of 3-nitro-o-phenylenediamine and 20.8 (0.10m) of phenanthrenequinone were refluxed in 1 l of 2B ethanol for about 2 hours. The precipitated product was collected and recrystallized from dimethylformamide to yield about 28.3 g. (87 percent yield) of 11-nitrodibenzo[a,c]phenazine, mp = 253°–255° C.

Analysis $C_{20}H_{11}N_3O_2$ MW 325. Calcd: C, 73.84; H, 3.41; N, 12.92; Found: C, 73.68; H, 3.68; N, 12.76.

B. 11-Aminodibenzo[a,c]phenazine

Sixteen and three tenths grams (0.05m) of 11-nitrobenzo[a,c]phenazine were hydrogenated at room temperature in 780 ml. of tetrahydrofuran with 4 g. of Raney nickel at 60 psi. After three equivalents of hydrogen were absorbed, the catalyst was filtered. The filtrate was evaporated in vacuo to provide a solid. The product was washed with ethanol to yield about 8.1 g.

(55 percent yield) of 11-aminodibenzo[a,c]phenazine, mp = 275° C. (dec.)

Analysis $C_{20}H_{13}N_3$ MW 295. Calcd: C, 81.34; H, 4.44; N, 14.23; Found: C, 81.09; H, 4.15; N, 13.97.

EXAMPLE 10

11-Chlorodibenzo[a,c]phenazine

When one tenth mole each of 4-chloro-o-phenylendiamine and phenanthrenequinone were reacted by the method of Example 7(A), 26 g. (83 percent yield) of 11-chlorodibenzo[a,c]phenazine, mp = 241–242° C. were obtained.

Analysis $C_{20}H_{11}ClN_2$ MW 314.5. Calcd: C, 76.31; H, 3.52; N, 8.90; Found: C, 76.02; H, 3.63; N, 8.69.

EXAMPLE 11

9-Chloroacenaphtho[1,2-b]quinoxaline

When 0.05 mole each of 4-chloro-o-phenylenediamine and acenaphthenequinone were reacted by the method of Example 7(A), 13 g. (90 percent yield) of 9-chloroacenaphtho[1,2-b]quinoxaline, mp = 224°–225° C., were obtained Analysis $C_{18}H_9ClN_2$ MW 288.5. Calcd: C, 74.88; H, 3.14; N, 9.70; Found: C, 74.56; H, 3.21; N, 9.57.

I claim:

1. The compound which is 9-(trifluoromethyl)acenaphtho[1,2-b]quinoxaline.

* * * * *